United States Patent
Takagi et al.

(10) Patent No.: US 7,160,731 B2
(45) Date of Patent: Jan. 9, 2007

(54) EXAMINATION METHOD OF BUFFER CAPACITY OF SALIVA AND EXAMINATION INSTRUMENT OF BUFFER CAPACITY OF SALIVA

(75) Inventors: Kazuhiro Takagi, Tokyo (JP); Junichi Okada, Tokyo (JP)

(73) Assignee: GC Corporation, Tokyo (JP)

( * ) Notice: Subject to any disclaimer, the term of this patent is extended or adjusted under 35 U.S.C. 154(b) by 376 days.

(21) Appl. No.: 10/241,645

(22) Filed: Sep. 12, 2002

(65) Prior Publication Data
US 2003/0059947 A1 Mar. 27, 2003

(30) Foreign Application Priority Data
Sep. 14, 2001 (JP) .............................. 2001-280025

(51) Int. Cl.
*G01N 31/16* (2006.01)
(52) U.S. Cl. ...................... 436/163; 436/162; 436/164; 436/169
(58) Field of Classification Search ................ 436/163, 436/162, 164, 169
See application file for complete search history.

(56) References Cited

U.S. PATENT DOCUMENTS 6,762,058 B1 * 7/2004 Takagi et al. ................ 436/163

FOREIGN PATENT DOCUMENTS

| JP | 357175129 A | * | 10/1982 |
| JP | 02002323493 A | * | 11/2002 |
| JP | 02003083961 A | * | 3/2003 |

OTHER PUBLICATIONS

G. Frostell, Swedish Dental Journal, vol. 4, No. 3, pp. 81-86, XP-009006557, "A Colourmetric Screening Test for Evaluation of the Buffer Capacity of Saliva", 1980.

S. Wikner, et al., Swedish Dental Journal, vol. 9, No. 2, pp. 45-47, XP-001145508, "A Clinical Evaluation of the Ability of the Dentobuff Method to Estimate Buffer Capacity of Saliva", 1985.

D. Ericson, et al., Scandinavian Journal of Dental Research, vol. 97, No. 5, pp. 405-407, XP-009006534, "Simplified Method to Estimate Salivary Buffer Capacity", 1989.

Derwent Publications, AN 1994-035504, XP-002244233, BR 9 301 846, Oct. 26, 1993.

A. Bardow, et al., Archives of Oral Biology, vol. 45, No. 1, pp. 1-12, XP-002244232, "The Buffer Capacity and Buffer Systems of Human Whole Saliva Measured Without Loss of $CO_2$", Jan. 2002.

* cited by examiner

*Primary Examiner*—Monique T. Cole
(74) *Attorney, Agent, or Firm*—Oblon, Spivak, McClelland, Maier & Neustadt, P.C.

(57) ABSTRACT

To provide a simple examination method of buffer capacity of saliva without influence by examiner's subjectivity and an examination instrument to carry out suitably the examination method, an examination instrument, in which two to ten kinds of chemical liquids each containing a pH indicator having a transition interval within a pH range of 3.0 to 7.0 and capable of easily discriminating its indicated color at two or more stages and an acid in an amount so as to exhibit a different pH value within a pH range of 1.5 or more but lower than 3.0 when water in the same amount as that of saliva to be examined is added at a temperature of 25° C. and a humidity of 50% are each immersed in a water-absorptive material, or are in a liquid or gel state and are accommodated within a constant-volume container, is prepared; saliva of a subject in a volume to be examined is added to each of the chemical liquids; after lapsing a predetermined time, the color of each chemical liquid is measured as a readily discriminable indicated color; and the buffer capacity of saliva is determined by overall evaluation from the readily discriminable indicated color as exhibited by the chemical liquid.

13 Claims, No Drawings

EXAMINATION METHOD OF BUFFER CAPACITY OF SALIVA AND EXAMINATION INSTRUMENT OF BUFFER CAPACITY OF SALIVA

BACKGROUND OF THE INVENTION

1. Field of the Invention

The present invention relates to an examination method of buffer capacity of saliva, by which the buffer capacity of saliva of a subject can be examined simply without being influenced by the subjectivity of an examiner and to an examination instrument of buffer capacity of saliva, with which the examination method of buffer capacity is suitably carried out.

2. Description of the Conventional Art

The forming and progress of dental caries occur in the following steps. That is, while demineralization wherein acids produced by the metabolism of hydrocarbons by bacteria in an oral cavity elute calcium ions and phosphate ions in teeth, and remineralization that is a phenomenon wherein the calcium ions and phosphate ions are again taken into the teeth, repeatedly act over a long period of time, a balance between the both is broken, and the environment is inclined to the demineralization side over a long period of time, whereby the dental caries is formed and progresses. The role of saliva includes not only a function to supply calcium ions and phosphate ions present in saliva to teeth but also a buffer capacity to neutralize acids produced by the metabolism of hydrocarbons by bacteria in an oral cavity, thereby preventing demineralization. Since there are observed differences in the buffer capacity of saliva against the acids individually, for making a guide for stopping the forming and progress of the dental caries, it is necessary to obtain objective information individually regarding the buffer capacity of saliva.

The buffer capacity of saliva is regulated mainly by the following three buffer functions: a function by the correlation between carbonic acid and a bicarbonate, a function by phosphates, and a function by proteins. Of these, the function by the correlation between carbonic acid and a bicarbonate is the most important, which is based on an equilibrium relation between carbonic acid and the bicarbonate. When an acid is added, the bicarbonate releases carbonic acid as a weak acid. This carbonic acid is rapidly decomposed into water and carbon dioxide, and then is liberated from the solution. In contrast to many buffering agents, this mechanism results in not accumulation of a weak acid but complete elimination of the acid. That is, in order that the buffer capacity of saliva based on the equilibrium relation between carbonic acid and the bicarbonate is maintained, it is considered that a sufficient amount of the bicarbonate for eliminating a large amount of the acid is needed. Further, it is already confirmed that the variation of the bicarbonate in saliva appears in a pH change of saliva.

Accordingly, for examining the buffer capacity of saliva, the evaluation of the amount of the bicarbonate through titration using an acid is the most confident, and its standard method at a laboratory level is the Ericsson's method (see Ericsson Y.; "Clinical investigations of the salivary buffering action", *Acta. Odontol. Scand.*, 17:131–65 (1959)). This Ericsson's method is a method in which a certain amount of hydrochloric acid is added to collected saliva, the mixture is stirred for a certain period of time while subjecting to a treatment for avoiding bubbling and inclusion of carbon dioxide, and then, the ultimate pH is measured by using electrodes. However, since this method requires a complicated operation and a specific device, it is not generally diffused.

Thus, as a method for examining the buffer capacity of saliva more simply, employed a method in which when saliva is dropped to a paper that has been previously immersed with an acid and a pH indicator and dried, by using a dropping pipette such that the saliva covers the whole of the paper, in the case where the buffer capacity acts against the acid immersed in the paper by the function between the carbonic acid and the bicarbonate in the saliva, and acts until the pH value reaches one exceeding a transition interval of the pH indicator immersed in the paper, the color exhibited by the pH indicator changes, and hence, the pH value of the paper having increased by the buffer capacity of the saliva is determined by comparing a color of the portion to which the saliva has been added with a color sample at a known pH, whereby the buffer capacity of saliva is examined according to three grades of low, medium and high (see Takashi KUMAGAYA, et al., *Clinical Cardiology*, 130–31, published by Ishiyaku Publishers, Inc.). However, this method involved a problem that since the buffer capacity of the saliva can be evaluated only according to the three grades of low, medium and high, it is not sufficient for more precious examination. Further, this method involved another problem that even a plurality of variations in the colors exhibited by the portion to which the saliva has been added are set up by immersing some kinds of pH indicators in a paper or other means in order to improve the precision of the examination, a scattering in the color determination by an examiner is so large that errors are likely caused.

SUMMARY OF THE INVENTION

The present invention is aimed to overcome the above-described problems of the conventional art techniques and to provide an examination method of buffer capacity of saliva, by which the buffer capacity of saliva of a subject can be examined simply without being influenced by the subjectivity of an examiner and an examination instrument of buffer capacity of saliva, with which the examination method of buffer capacity is suitably carried out.

In order to achieve the above-described aim, we, the present inventors made extensive and intensive investigations. As a result, they have found the following matters. That is, plural kinds of chemical liquids each comprising a pH indicator having a transition interval within a pH range to be used for the measurement and capable of easily discriminating its indicated color at two or more stages and an acid in an amount so as to exhibit a pH value within a range lower than the pH value of the transition interval of the pH indicator when water in the same amount as the volume of saliva to be used for the examination is added are prepared, and the amount of the acid in each chemical liquid is made different. And, in the case where the saliva to be examined has a high buffer capacity, even when the amount of the acid in the chemical liquid is low, or the amount of the acid in the chemical liquid is high, the buffer capacity acts until the pH value reaches one exceeding the transition interval of the pH indicator due to the added saliva, whereby the indicated color of the pH indicator changes. On the other hand, in the case where the saliva to be examined has a low buffer capacity, in the chemical liquid in which the amount of the acid is low, the buffer capacity acts until the pH value reaches one exceeding the transition interval of the pH indicator due to the saliva added, whereby the indicated color of the pH indicator changes, whereas in the chemical liquid in which the amount of the acid is high, the buffer capacity does not act until the pH value reaches one exceeding the transition interval of the pH indicator due to the added saliva, whereby the indicated color of the pH indicator does not change. By utilizing such matters, it has been found that by merely setting up an indicated color capable of being easily discriminated at two or more stage for one chemical liquid, the buffer capacity of saliva can be determined without causing differences among individuals in the determination of each color and that even when various variations are not set up for the indicated color of one chemical liquid after the addition of saliva, the buffer capacity of saliva of an individual subject can be simply and preciously examined without being influenced by the subjectivity of an examiner.

Specifically, the present invention relates to an examination method of buffer capacity of saliva, which comprises preparing two to ten kinds of chemical liquids each comprising a pH indicator having a transition interval within a pH range of 3.0 to 7.0 and capable of easily discriminating its indicated color at two or more stages and an acid in an amount so as to exhibit a different pH value within a pH range of 1.5 or more but lower than 3.0 when water in the same amount as the volume of saliva to be used for the examination is added under conditions at a temperature of 25° C. and at a humidity of 50%; adding saliva of a subject in a volume to be used for the examination to each of the chemical liquids; measuring a color of each chemical liquid after lapsing a predetermined period of time as the indicated color to be easily discriminated; and determining the buffer capacity of saliva through overall evaluation from the indicated color to be easily discriminated as exhibited by each chemical liquid. The present invention also relates to an examination instrument of buffer capacity of saliva, in which water-absorptive materials are each immersed with the chemical liquid and immobilized in a non-water-absorptive material at intervals and an examination instrument of buffer capacity of saliva, in which the chemical liquids are in a liquid or gel state and are accommodated by a constant volume respectively within a constant-volume containers, integrated in series the both examination instruments of buffer capacity of saliva being suitable for carrying out the examination method of buffer capacity of saliva.

DESCRIPTION OF THE PREFERRED EMBODIMENTS

In the examination method of buffer capacity of saliva according to the present invention are used two to ten kinds of chemical liquids each comprising a pH indicator having a transition interval within a pH range of 3.0 to 7.0 and capable of easily discriminating its indicated color at two or more stages and an acid in an amount so as to exhibit a different pH value within a pH range of 1.5 or more but lower than 3.0 when water in the same amount as the volume of saliva to be used for the examination is added under conditions at a temperature of 25° C. and at a humidity of 50%.

The pH indicator that is used for the chemical liquid is not particularly limited, so far as it has a transition interval within a pH range of 3.0 to 7.0 and can easily discriminate its indicated color at two or more stages. For example, Bromophenol Blue (transition interval: 3.0 to 4.6), Bromochlorophenol Blue (transition interval: 3.2 to 4.8), Congo Red (transition interval: 3.0 to 5.0), Bromocresol Green (transition interval: 3.8 to 5.4), 2,5-dinitrophenol (transition interval: 4.0 to 5.8), Methyl Red (transition interval: 4.4 to 6.2), Chlorophenol Red (transition interval: 5.0 to 6.6), p-nitrophenol (transition interval: 5.0 to 7.0), Bromocresol Purple (transition interval: 5.2 to 6.8), Bromophenol Red (transition interval: 5.2 to 7.0), and Bromothymol Blue (transition interval: 6.0 to 7.0) are preferred because they have a transition interval within a pH range of 3.0 to 7.0. The reason why the pH indicator must have a transition interval within a pH range of 3.0 to 7.0 resides in the matter that since what is important in the buffer capacity of saliva is a function by the correlation between carbonic acid and a bicarbonate, the measurement is carried out in the acidic side. These pH indicators can be used in admixture of two or more thereof. The pH indicator is used upon being dissolved in a solvent such as water and ethanol.

As the acid that can be used for the chemical liquid are employable general acids such as hydrochloric acid, sulfuric acid, nitric acid, nitrous acid, citric acid, oxalic acid, formic acid, phosphoric acid, malonic acid, sulfamic acid, phthalic acid, succinic acid, maleic acid, folic acid, malic acid, tartaric acid, boric acid, pyruvic acid, alginic acid, hyaluronic acid, uric acid, and acrylic acid. Of these acids are preferred hydrochloric acid, sulfuric acid and phosphoric acid because they can give rise to stable examination results and are readily available. The acid is used upon being dissolved in a solvent such as water and ethanol, like the pH indicator.

The chemical liquid comprising a pH indicator and an acid as described above is used in a liquid or gel state, or in the way that it is immersed in a water-absorptive material of a predetermined volume by means such as immersing or spraying. In the case where the chemical liquid is used in a liquid or gel state, it is accommodated within a container of a predetermined volume, which is made of a glass or a polymer such as polypropylene, polystyrene and polyethylene, and then put into use. In the case where the chemical liquid is immersed in a water-absorptive material of a predetermined volume, it is immersed in a water-absorptive material in a strip-like, cylindrical or square pillar-like form and then put into use. Alternatively, such water-absorptive materials of a predetermined volume, having the chemical liquid immersed therein, are immobilized in a non-water-absorptive material at intervals and then put into use.

In the case where the chemical liquid is immersed in the water-absorptive material of a predetermined volume and then put into use, the water-absorptive material is not particularly limited, so far as it can immerse the chemical liquid therein. Examples include papers such as filter paper, blotting paper, and paper towel; cloths and non-woven fabrics made of, e.g., absorbent cotton, quartz wool, glass wool, wool, silk, cotton, linen, acrylic fibers, rayon, nylon, nitrocellulose, cellulose acetate, regenerated cellulose, or glass fibers; and solid moldings of, e.g., dextran, mutan, levan, or cellulose powder. Of these, papers such as filter paper, blotting paper, and paper towel are suitable. Further, in the case where such water-absorptive materials of a predetermined volume, having the chemical liquid immersed therein, are immobilized in a non-water-absorptive material at intervals and then put into use, those materials shaped in a plate-like form such as a strip-like or disc-like form, which are made of a glass or a polymer such as polypropylene, polystyrene, and polyethylene, can be suitably used as the non-water-absorptive material to be used.

The amount of the acid in the chemical liquid comprising a pH indicator and an acid as used in this manner is one such that it exhibits a different pH value within a pH range of 1.5 or more but lower than 3.0 when water in the same amount as the volume of saliva to be used for the examination is added under conditions at a temperature of 25° C. and at a humidity of 50%. If the pH value is lower than 1.5 when water in the same amount as the volume of saliva to be used for the examination is added under conditions at a temperature of 25° C. and at a humidity of 50%, in the case where the buffer capacity of saliva to be examined is low, the pH value of all the chemical liquids having saliva of a subject in a volume to be used for the examination added thereto does not reach the transition interval of the pH indicator, so that the indicated color may not change. On the other hand, if it is 3.0 or more, even in the case where the buffer capacity of saliva to be examined is high, the pH value of all the chemical liquids having saliva of a subject in a volume to be used for the examination added thereto exceeds the transition interval of the pH indicator, so that such is not practically useful.

The reason why the kind of the chemical liquids having a varied amount of the acid must be two to ten is as follows. That is, in the case where the kind of the chemical liquid is one, the amount of the acid can be set up only at one stage, so that a sufficient precision in the examination results is not obtained. On the other hand, in the case where the kind of the chemical liquids is eleven or more, combination patterns of the indicated colors of the chemical liquids are so many that judgment becomes complicated, and hence, such is not desired.

In carrying out the examination method of buffer capacity of saliva according to the present invention, two to ten kinds of chemical liquids each comprising a pH indicator having a transition interval within a pH range of 3.0 to 7.0 and capable of easily discriminating its indicated color at two or more stages and an acid in an amount so as to exhibit a different pH value within a pH range of 1.5 or more but lower than 3.0 when water in the same amount as the volume of saliva to be used for the examination is added under conditions at a temperature of 25° C. and at a humidity of 50% are prepared; and a predetermined amount of saliva of a subject is added to the thus prepared chemical liquids by using a dropping pipette or other means.

During this time, in the case where each of the chemical liquids is in a liquid or gel state, and its predetermined volume is accommodated within a container, it is preferred that after adding a predetermined amount of saliva by using a dropping pipette or other means, the chemical liquid and the saliva are thoroughly stirred within the container. Accordingly, it is preferred that each of the containers can be sealed by a lid. But, there may be employed a structure in which a plastic film or the like for sealing is previously fixed to the container by means of heat fusion or the like such that the chemical liquid within the container does not leak, and the plastic film or the like for sealing is peeled off from an opening of the container at the time of the examination of saliva. In the case of such a structure, when the respective containers are arranged in series, the indicated colors of the respective chemical liquids can be compared with each other, and hence, such is convenient. Further, for example, when a line showing a necessary amount of saliva to be added is designated in each container, or when the container is configured so as to become full when a necessary amount of saliva is added, it is simple to add the necessary amount of saliva.

In the case where each of the chemical liquids is immersed in the water-absorptive material of a predetermined volume, when after adding saliva so as to cover the whole of the water-absorptive material, the remaining saliva without being absorbed in the water-absorptive material is absorbed by a paper towel or the like, the amount of saliva to be added can be made constant. During this time, when the water-absorptive materials of a predetermined volume, having the chemical liquid immersed therein, are immobilized in a non-water-absorptive material at intervals, the indicated colors of the respective chemical liquids can be compared with each other, and hence, such is convenient. Further, it is preferred that each of the water-absorptive materials has the same volume.

Thus, saliva of a subject of a predetermined volume to be used for the examination is added to each of the chemical liquids; after lapsing a predetermined period of time of 1 to 30 minutes, the color of each chemical liquid is measured as the readily discriminable indicated color; and the buffer capacity of saliva is determined by overall evaluation from the readily discriminable indicated color as exhibited by the chemical liquid.

The overall evaluation is carried out in the following manner. That is, for example, a score of buffer capacity of saliva is previously set up for the indicated color as exhibited by each chemical liquid, which is easily discriminated at two or more stages; and by using the thus obtained scores of buffer capacity of saliva, a treatment of adding them or averaging them is applied; and the buffer capacity of saliva is determined from the results, thereby examining the buffer capacity of saliva. At this time, in the case where the pH indicator to be used for the chemical liquid is, for example, Bromocresol Green, since the color changes as yellow→green→blue, the score of buffer capacity of saliva can be set up at 0 point for yellow, 1 point for green, and 2 points for blue, respectively. Further, in the case where the pH indicator is Methyl Red, since the color changes as red→orange→yellow, the score of buffer capacity of saliva can be set up at 0 point for red, 1 point for orange, and 2 points for yellow, respectively.

In addition, the overall evaluation may be carried out in the following manner. That is, the magnitude of the buffer capacity of saliva is determined from a color combination table summarizing combinations of the indicated color of each of the chemical liquids after adding saliva and lapsing a predetermined period of time, or scores of buffer capacity of saliva are previously given to the color combinations and the buffer capacity of saliva are determined from the obtained scores of buffer capacity of saliva, thereby examining the buffer capacity of saliva. At this time, with respect to the score of buffer capacity of saliva, for example, in the case where three kinds of chemical liquids are used, and pH indicators for the chemical liquids are all Bromocresol Green, the score of buffer capacity of saliva can be set up at 1 point for yellow-yellow-yellow, 2 points for yellow-yellow-green, 3 points for yellow-green-green, 4 points for yellow-green-blue, 5 points for green-green-green, 6 points for green-green-blue, 7 points for green-blue-blue, and 8 points for blue-blue-blue, respectively. Further, for example, in the case where three kinds of chemical liquids are used, and pH indicators for the chemical liquids are all Methyl Red, the score of buffer capacity of saliva can be set up at 1 point for red-red-red, 2 points for red-red-orange, 3 points for red-orange-orange, 4 points for red-orange-yellow, 5 points for orange-orange-orange, 6 points for orange-orange-yellow, 7 points for orange-yellow-yellow, and 8 points for yellow-yellow-yellow, respectively.

The invention will be described below in more detail with reference to the following Examples, but it should not be construed that the invention is limited thereto.

EXAMPLE 1

A solution as pH the indicators, prepared by mixing, a Bromocresol Green solution (0.5 g/L) and a Methyl Red solution (0.5 g/L) in a ratio of 1:1 was adjusted at a pH value of 3.0, 3.2 and 3.4, respectively with phosphoric acid as the acid. Each of the thus prepared solutions was immersed in a filter paper (a trade name: Chromatographic Filter Paper No. 514A, available from Advantec Toyo Kaisha, Ltd.) having a width of 6 mm, a length of 6 mm and a thickness of 0.32 mm as the water-absorptive material, followed by drying. The resulting three pieces (1) to (3) were stuck to a polyethylene plate having a thickness of 0.5 mm, a width of 6 mm and a length of 70 mm as the strip-like non-water-absorptive material and immobilized at predetermined intervals, to prepare an examination instrument of buffer capacity of saliva. At this time, all of the pieces (1) to (3) were colored red. Further, ion-exchanged water was added to each of the pieces (1) to (3) under conditions at a temperature of 25° C. and at a humidity of 50%, and excessive water was lightly wiped out. As a result, the pieces (1) to (3) exhibited a pH value of 2.0, 1.8 and 1.6, respectively.

Each of saliva of five subjects A to E was added to each of the pieces (1) to (3), and excessive saliva was lightly wiped out. Five minutes later, the pieces exhibited any one of red, blue and green colors. Thus, points were summed as 0 point for red, 1 point for blue, and 2 points for green, respectively. The results obtained are shown in Table 1. Further, bicarbonate concentrations in saliva of the five subjects A to E as measured by the titration using hydrochloric acid are also shown in Table 1.

TABLE 1

| Subject | Color and score of piece (1) | Color and score of piece (2) | Color and score of piece (3) | Total score | Bicarbonate concentration (mM) |
|---|---|---|---|---|---|
| A | Blue 1 point | Blue 1 point | Red 0 point | 2 points | 5 |
| B | Green 2 points | Green 2 points | Blue 1 point | 5 points | 20 |
| C | Green 2 points | Blue 1 point | Blue 1 point | 4 points | 15 |
| D | Green 2 points | Blue 1 point | Red 0 point | 3 points | 10 |
| E | Green 2 points | Green 2 points | Green 2 points | 6 points | 25 |

EXAMPLE 2

In the examination of buffer capacity of saliva in Example 1, the buffer capacity of saliva was determined from the color combinations of the pieces (1) to (3) in that order, while setting up the score of buffer capacity of saliva at 1 point for red-red-red, 2 points for blue-red-red, 3 points for blue-blue-red, 4 points for green-blue-red, 5 points for blue-blue-blue, 6 points for green-blue-blue, 7 points for green-green-blue, and 8 points for green-green-green, respectively. The examination results are shown in Table 2. Further, bicarbonate concentrations in saliva of the five subjects A to E as measured by the titration using hydrochloric acid are also shown in Table 2.

TABLE 2

| Subject | Color and score of piece (1) | Color and score of piece (2) | Color and score of piece (3) | Score of buffer capacity of saliva | Bicarbonate concentration (mM) |
|---|---|---|---|---|---|
| A | Blue | Blue | Red | 3 points | 5 |
| B | Green | Green | Blue | 7 points | 20 |
| C | Green | Blue | Blue | 6 points | 15 |
| D | Green | Blue | Red | 4 points | 10 |
| E | Green | Green | Green | 8 points | 25 |

EXAMPLE 3

Three bores having a diameter of 7 mm were provided on a polyethylene plate having a thickness of 5 mm, a width of 6 mm and a length of 70 mm at predetermined intervals. Into the bores were inserted and placed three containers (1) to (3) of a microtube (made by Iwaki Glass Co., Ltd.) having a volume of 1.5 ml, each containing a chemical liquid consisting of 50 μl of a Bromocresol Green solution (0.5 g/L) as the pH indicator and 50 μl of 0.18 N, 0.30 N or 0.42 N hydrochloric acid as the acid to prepare an examination instrument of buffer capacity of saliva. At this time, all of the chemical liquids within the containers (1) to (3) were colored yellow. Further, 1 ml of ion-exchanged water was added to each of the containers (1) to (3) under conditions at a temperature of 25° C. and at a humidity of 50%. As a result, the chemical liquids within the containers (1) to (3) exhibited a pH value of 1.7, 1.8 and 2.1, respectively.

One milliliter of saliva of each of five subjects A to E was added to each of the chemical liquids within the containers (1) to (3), and after closing a lid, each of the mixtures was well stirred. Five minutes later, the indicated colors of the respective chemical liquids were any one of yellow, green, and blue colors. Thus, points were summed as 0 point for yellow, 1 point for green, and 2 points for blue, respectively. The results obtained are shown in Table 3. Further, bicarbonate concentrations in saliva of the five subjects A to E as measured by the titration using hydrochloric acid are also shown in Table 3.

TABLE 3

| Subject | Color and score of container (1) | Color and score of container (2) | Color and score of container (3) | Total score | Bicarbonate concentration (mM) |
|---|---|---|---|---|---|
| A | Green 1 point | Yellow 0 point | Yellow 0 point | 1 point | 5 |
| B | Blue 2 points | Green 1 point | Green 1 point | 4 points | 20 |
| C | Blue 2 points | Green 1 point | Yellow 0 point | 3 points | 15 |
| D | Green 1 point | Green 1 point | Yellow 0 point | 2 points | 10 |
| E | Blue 2 points | Blue 2 points | Green 1 point | 5 points | 25 |

EXAMPLE 4

Seven bores having a diameter of 7 mm were provided on a polyethylene plate having a thickness of 5 mm, a width of 6 mm and a length of 70 mm at predetermined intervals. Into the bores were inserted and placed seven containers (1) to (7) of a microtube (made by Iwaki Glass Co., Ltd.) having a volume of 1.5 ml, each containing a chemical liquid consisting of 50 μl of a Bromocresol Green solution (0.5 g/L) as the pH indicator and 50 μl of 0.12 N, 0.18 N, 0.24 N, 0.30 N, 0.36 N, 0.42 N or 0.48 N hydrochloric acid as the acid to prepare an examination instrument of buffer capacity of saliva. At this time, all of the chemical liquids within the containers (1) to (7) were colored yellow. Further, 1 ml of ion-exchanged water was added to each of the containers (1) to (7) under conditions at a temperature of 25° C. and at a humidity of 50%. As a result, the chemical liquids within the containers (1) to (7) exhibited a pH value of 2.22, 2.05, 1.92, 1.82, 1.74, 1.68, and 1.62, respectively.

One milliliter of saliva of each of five subjects A to E was added to each of the chemical liquids within the containers (1) to (7), and after closing a lid, each of the mixtures was well stirred. Five minutes later, the indicated colors of the respective chemical liquids were any one of yellow, green, and blue colors. Thus, points were summed as 0 point for yellow, 1 point for green, and 2 points for blue, respectively. The results obtained are shown in Table 4. Further, bicarbonate concentrations in saliva of the five subjects A to E as measured by the titration using hydrochloric acid are also shown in Table 4.

dental caries of a subject simply and preciously without being influenced by the subjectivity of an examiner. Accordingly, the present invention is greatly valuable in contribution to the dental remedy field. In addition, by utilizing this principle, the present invention is applicable to blood and aqueous solutions, and is greatly valuable in contribution to not only the dental remedy field but also various fields including all medical treatments, examination of water, and preparation of reagents.

While the present invention has been described in detail and with reference to specific embodiments thereof, it will be apparent to one skilled in the art that various changes and modifications can be made therein without departing from the spirit and scope thereof.

What is claimed is:

1. A method for determining the buffering capacity of saliva, comprising:
    adding a sample of saliva to each of two or more containers that contain a liquid or gel of predetermined volume,
    wherein each liquid or gel comprises at least one pH indicator and a different concentration of acid,
    wherein said different concentrations of acid are selected to provide a different pH value for each liquid or gel within the pH range of 1.5 to 3.0 when a volume of water equal to the volume of saliva is added at a temperature of 25° C. and a humidity of 50%, and
    wherein the at least one pH indicator exhibits a color transition interval within the pH range of 3.0 to 7.0;

TABLE 4

| Subject | Color and score of container (1) | Color and score of container (2) | Color and score of container (3) | Color and score of container (4) | Color and score of container (5) | Color and score of container (6) | Color and score of container (7) | Total score | Bicarbonate concentration (mM) |
|---|---|---|---|---|---|---|---|---|---|
| A | Green 1 point | Green 1 point | Green 1 point | Green 1 point | Green 1 point | Yellow 0 point | Yellow 0 point | 5 | 5 |
| B | Blue 2 points | Blue 2 points | Blue 2 points | Blue 2 points | Green 1 point | Green 1 point | Yellow 0 point | 10 | 20 |
| C | Blue 2 points | Blue 2 points | Green 1 point | Green 1 point | Green 1 point | Green 1 point | Yellow 0 point | 8 | 15 |
| D | Blue 2 points | Green 1 point | Green 1 point | Green 1 point | Green 1 point | Green 1 point | Yellow 0 point | 7 | 10 |
| E | Blue 2 points | Blue 2 points | Blue 2 points | Blue 2 points | Green 1 point | Green 1 point | Green 1 point | 11 | 25 |

As described above in detail, the examination method of buffer capacity of saliva and the examination instrument of buffer capacity of saliva according to the present invention enables one to carry out an examination of saliva necessary for making a guide for stopping the forming and progress of determining the color change of each liquid or gel contacted with the saliva sample;
wherein the relative color change of each liquid or gel after the addition of the saliva sample is indicative of the buffering capacity of the saliva sample.

2. The method of claim 1, which comprises adding the saliva sample to two or more containers that contain a liquid of predetermined volume, wherein each liquid comprises at least one pH indicator and a different concentration of acid.

3. The method of claim 1, which comprises adding the saliva sample to two or more containers that contain a gel of predetermined volume, wherein each gel comprises at least one pH indicator and a different concentration of acid.

4. The method of claim 1, wherein said container is at least one non-water-absorptive material selected from the group consisting of glass, polypropylene, polystyrene and polyethylene.

5. The method of claim 1, wherein each liquid or gel comprises at least one pH color indicator selected from the group consisting of Bromophenol Blue, Bromochlorophenol Blue, Congo Red, Bromocresol Green, 2,5-dinitrophenol, Methyl Red, Chlorophenol Red, Bromocresol Purple, Bromophenol Red, and Bromothymol Blue.

6. The method of claim 1, wherein the acid in said liquid or gel is selected from at least one of the group consisting of hydrochloric acid, sulfuric acid and phosphoric acid.

7. The method of claim 1, wherein each liquid or gel contains a single pH color indicator.

8. The method of claim 1, wherein each liquid or gel contains more than one pH color indicator.

9. A method for determining the buffering capacity of saliva, comprising:
adding a sample of saliva to each of two or more water-absorptive materials of predetermined volume so as to cover the whole of each water-absorptive materials which each comprise at least one pH indicator and a different concentration of acid,
wherein said different concentrations of acid are selected to provide a different pH value for each water-absorptive materials within the pH range of 1.5 to 3.0 when a volume of water equal to the volume of saliva is added at a temperature of 25° C. and a humidity of 50%, and
wherein the at least one pH indicator exhibits a color transition interval within the pH range of 3.0 to 7.0;
determining the color change of each water-absorptive materials contacted with the saliva sample;
wherein the relative color change of each water-absorptive materials after the addition of the saliva sample is indicative of the buffering capacity of the saliva sample.

10. The method of claim 9, wherein said water-absorptive material is selected from the group consisting of paper, cloth, non-woven fabric, and solid molding.

11. The method of claim 9, wherein each water-absorptive material comprises at least one pH color indicator selected from the group consisting of Bromophenol Blue, Bromoclorophenol Blue, Congo Red, Bromocresol Green, 2,5-dinitrophenol, Methyl Red, Chlorophenol Red, Bromocresol Purple, Bromophenol Red, and Bromothymol Blue.

12. The method of claim 9, wherein the acid in said water-absorptive material is selected from at least one of the group consisting of hydrochloric acid, sulfuric acid and phosphoric acid.

13. The method of claim 9, wherein each water-absorptive material contains a single pH color indicator.

* * * * *